US006947866B2

(12) United States Patent
Staab (10) Patent No.: US 6,947,866 B2
(45) Date of Patent: Sep. 20, 2005

(54) APPARATUS AND METHOD FOR HANDHELD SAMPLING

(75) Inventor: Torsten A. Staab, Whiterock, NM (US)

(73) Assignee: The Regents of the University of California, Los Alamos, NM (US)

( * ) Notice: Subject to any disclaimer, the term of this patent is extended or adjusted under 35 U.S.C. 154(b) by 0 days.

(21) Appl. No.: 10/720,955

(22) Filed: Nov. 24, 2003

(65) Prior Publication Data

US 2005/0187733 A1    Aug. 25, 2005

(51) Int. Cl.⁷ .......................... G06F 15/00; G06F 17/00
(52) U.S. Cl. ...................................... 702/150; 235/375
(58) Field of Search ............................... 702/150, 187; 250/428, 336.1, 435; 235/375

(56) References Cited

U.S. PATENT DOCUMENTS

| 4,464,574 A | * | 8/1984 | Vandrish ............... 250/432 PD |
| 4,550,381 A | * | 10/1985 | Waechter et al. ........... 250/369 |
| 5,468,968 A | | 11/1995 | Bailey et al. ............... 250/435 |
| 5,591,974 A | | 1/1997 | Troyer et al. ............ 250/336.1 |
| 5,864,784 A | * | 1/1999 | Brayton et al. ............. 702/187 |
| 6,228,657 B1 | * | 5/2001 | Genovese et al. ........... 436/167 |
| 6,659,338 B1 | * | 12/2003 | Dittmann et al. ........... 235/375 |
| 6,771,802 B1 | * | 8/2004 | Patt et al. .................. 382/128 |
| 2004/0232323 A1 | * | 11/2004 | Bosco et al. ................ 250/253 |

OTHER PUBLICATIONS

Mann, Humanistic Computing: "WearComp" as a New Framework and Application for Intelligent Signal Processing, Nov. 1998, 1998 IEEE, vol. 86, No. 11, pp. 2123-2151.*
Brills et al., Remote Sensing Tools Assist in Environmental Forensics: Part II- Digital Tools, Environmental Forensics 2001.*

* cited by examiner

*Primary Examiner*—John Barlow
*Assistant Examiner*—Toan M. Le
(74) *Attorney, Agent, or Firm*—Mark N. Fitzgerald (57) ABSTRACT

The present invention includes an apparatus, and corresponding method, for taking a sample. The apparatus is built around a frame designed to be held in at least one hand. A sample media is used to secure the sample. A sample media adapter for securing the sample media is operated by a trigger mechanism connectively attached within the frame to the sample media adapter.

21 Claims, 6 Drawing Sheets

APPARATUS AND METHOD FOR HANDHELD SAMPLING

STATEMENT REGARDING FEDERAL RIGHTS

This invention was made with government support under Contract No. W-7405-ENG-36 awarded by the U.S. Department of Energy. The government has certain rights in the invention.

FIELD OF THE INVENTION

The present invention relates generally to sampling and subsequent cataloging of sampling data and, more particularly, to a handheld sampling apparatus capable of electronically logging sample-related multi-media data.

BACKGROUND OF THE INVENTION

In today's forensic evidence collection, the majority of time is spent with manually recording sample collection-related information, such as sampling location, time, date, sampled objects, sample storage container ID, sampler ID, and the like. In most cases, the sample collection-related record keeping is done by hand using a variety of incompatible media types, e.g., pen and paper, a digital camera, and a voice recorder. This leaves the sample collector with a set of disparate, unconnected multi-media data sets. Before the collected sample can be processed in the laboratory, those multi-media sample records must be manually merged into a unified electronic sample record/report. This data fusion usually takes place upon the return of the sample collector from the field. Besides being time-consuming and costly, the data fusion process is error prone due to transcription errors and missing records.

U.S. Pat. No. 5,591,974, issued on Jan. 7, 1997, to Troyer et al., teaches a method for automated collection and processing of environmental sample. The '974 invention is primarily designed for sampling of nuclear radiation levels at identified distributed locations within nuclear facilities. Bar coded sample collectors are deployed and their respective codes are read using a portable data entry apparatus that also records the time of deployment. The time and sample collector ID are cross referenced in memory in the portable apparatus. Similarly, when later recovering the sample collector, the bar code is again read and the time of collection is stored as indexed to the sample collector. The identity of the operator may also be encoded and stored. The data is then be transmitted to a base processor from the portable data entry apparatus. The sample testing results are then similarly recorded and transmitted to the base processor, coupling the sample results with the previous logged information.

Similar to the '974 patent, supra, U.S. Pat. No. 5,468,968, issued on Nov. 21, 1995, to Bailey et al., teaches a system and method for the collection and use of radiation sampling data on airborne particulate materials that includes enhanced data accuracy, security, retrievability, accountability of personnel, and chain of custody information. The '968 system uses bar coding on a collection means to properly identify the sample and downloads the information onto a computer means for receiving and processing the sample data. The computer means also correlates the collection data with the subsequent analysis information on the procured samples.

The present invention does not require the operator to physically touch or interact with the taken samples. Through use of a unique, universal multi-media sample adapter, the present invention provides "hands-off" sample media loading and unloading, which prevents contamination of both the sample and the operator. A universal sample adapter allows the use of a wide variety of sampling media formats of any shape and size (e.g., vials, nasal swabs, foams, bags, filter papers, contact plates, air cassettes, and the like). Thus, the present invention may sample and collect solids, liquids, and gases.

Various objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

In accordance with the purposes of the present invention, as embodied and broadly described herein, the present invention includes an apparatus, and corresponding method, for taking a sample. The apparatus is built around a frame designed to be held in at least one hand. A sample media is used to secure the sample. A sample media adapter for securing the sample media is operated by a trigger mechanism connectively attached within the frame to the sample media adapter.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings.

DETAILED DESCRIPTION

The present invention comprises an apparatus and corresponding method to take, process, and catalog solid, liquid, or gaseous samples. In various embodiments, the present invention comprises: a universal sample media adapter; either a global position system (GPS) or a 3-dimensional magnetic, ultrasonic, or laser-based position tracking system, to associate a taken sample with the respective sample location; a digital camera, or similar picture and video capable mechanism, providing images of the sample, sample location, and the physical collection process; a microphone and recorder for capturing voice descriptions and information; and, an onboard computer operating system that electronically stores and correlates all the sample information. These various embodiments support the acquisition of textual, numerical, graphical, video, and voice-attributed sample identification data. Handwritten identification data, which is still commonly used in field sampling operations may also be processed and electronically recorded, providing greater flexibility to the operator.

A few of the envisioned users for the present invention include emergency response teams, law enforcement forensics units, health care providers, the U.S. Customs department, supply chain safety inspectors, environmental monitoring organizations, U.S. military departments, the Federal Bureau of Investigation, the Center for Disease Control and Prevention, and the Federal Food and Drug Administration.

In accordance with one embodiment of the present invention, a handheld sampling apparatus, is used to rapidly collect a variety of samples both in indoor and outdoor environments. While collecting the samples, the apparatus electronically registers and links the sample to the corresponding sample location. Thus, the apparatus automatically provides a record of the full chain of custody, which is especially important for applications like forensic evidence collection. The automatically recorded sample location information enables the operator to return to the specific sampling location, should re-sampling be required at a later point, without having to physically mark or manually record the location. These features allow sampling in unstructured, previously unknown or un-mapped locations, while gathering a significant amount of reproducible, site-specific information to attribute to the collected sample.

Through a universal adapter mechanism, the sampling apparatus can support a wide variety of sampling media, such as filters, swipes, foams, swabs, vials, air cassettes, and the like. The universal adapter enables the operator taking the sample to quickly reconfigure the apparatus and take different types of samples, such as liquids, solids, or gases, with the same apparatus. The sampling probe/media can be quickly loaded and unloaded without touching the sample media and sample, thereby eliminating any potential for sample cross-contamination or personnel contamination.

In one embodiment, the sampling apparatus is equipped with a voice recognition feature that enables the operator to perform apparatus operations via voice commands, to include electronic recording of a sampling location or automatic identification of a barcode label. The capability of recording vital sampling data without having to physically touch the sample apparatus prevents the apparatus from getting accidentally contaminated and allows the sampler to have one hand free at all times.

Figure 1:
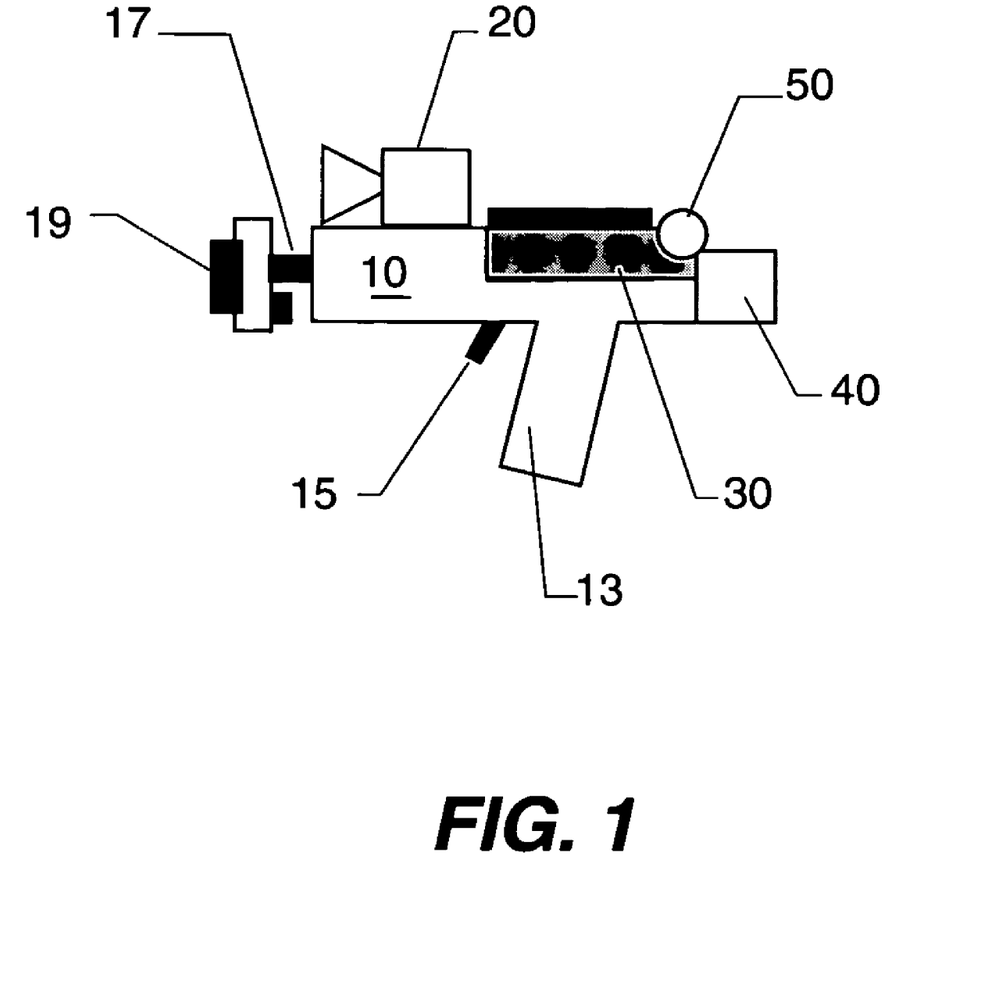
FIG. 1 is a pictorial illustration of the present invention.

Referring now to one embodiment portrayed in FIG. 1, the sampling apparatus is designed to appear like a handheld gun. Apparatus frame 10 includes: pistol grip 13, trigger mechanism 15, and universal sample media adapter 17. Universal sample media adapter 17 allows for single-handed loading and unloading of sampling media 19 and supports a wide variety of standard as well as proprietary sampling media formats, such as filters, swipes, contact plates, air cassettes, foams, swaps, and vials. Adapter 17 prevents the potential contamination of the handheld apparatus by a sample and prevents potential sample cross-contamination. When the operator is finished taking the sample, media 19 is dropped into a sample container by simply pressing trigger 15.

Figure 2A:
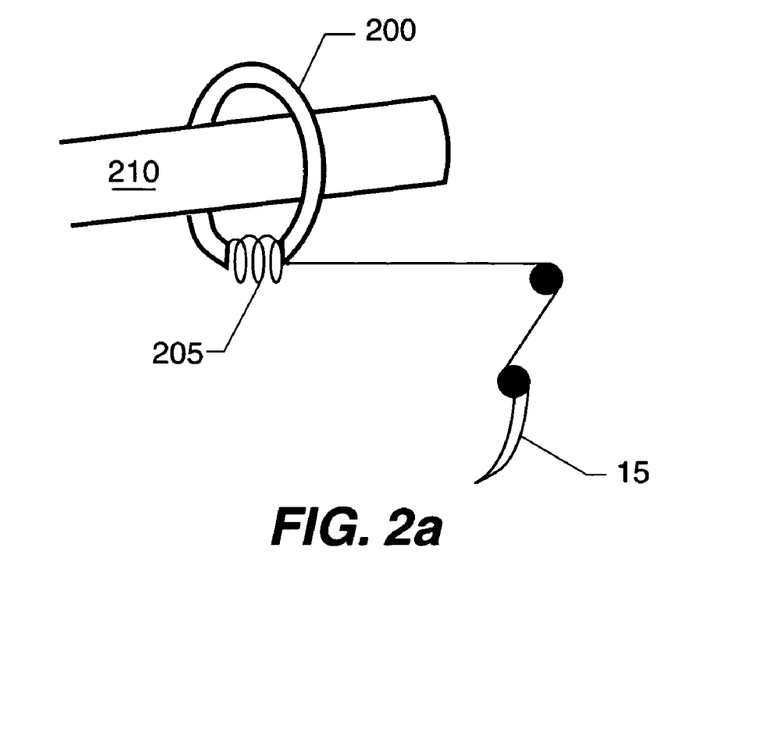
FIGS. 2a, 2b, 2c, and 2d are pictorial illustrations of various trigger mechanisms for operating a universal sample media adapter.

Various trigger mechanisms may be employed to link trigger 15 with adapter 17; FIGS. 2a, 2b, 2c, and 2d illustrate several designs. In FIG. 2a, circular band 200 includes spring 205 which is elongated when trigger 15 is depressed. Member 210 extending from sampling media 19 slides into circular band 200. When trigger 15 is released, spring 205 reduces the circumference of circular band 200 to firmly secure member 210. Once the sample is taken, trigger 15 is depressed, spring 205 relaxes, and band 200 releases member 210.

Figure 2B:
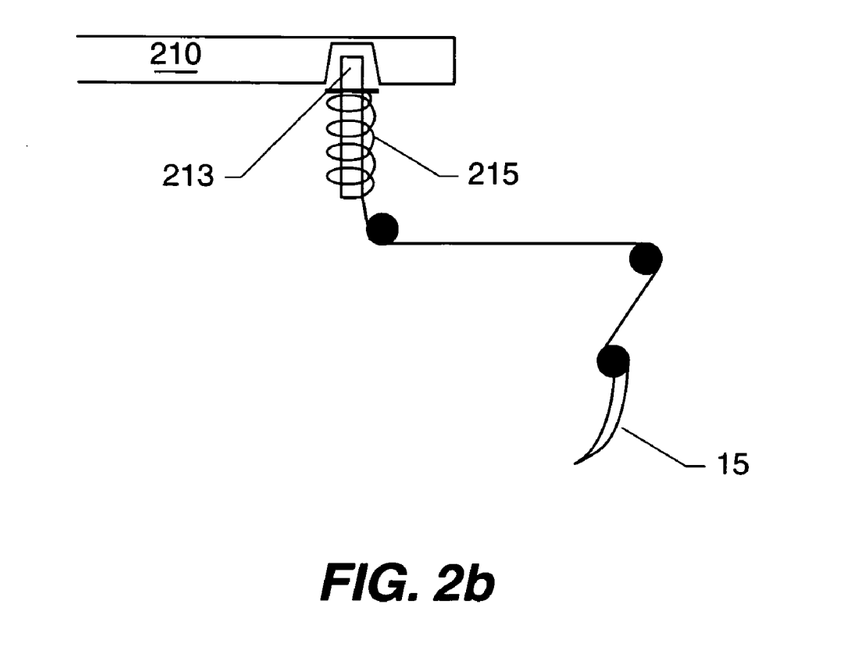

In FIG. 2b, spring-loaded pin 215 is pulled away from member 210 by depressing trigger 15 and, thus, compressing spring 215. Once trigger 15 is released, spring-loaded pin 215 moves upward into notch 213 as spring 217 un-compresses, thus securing member 210.

Figure 2C:
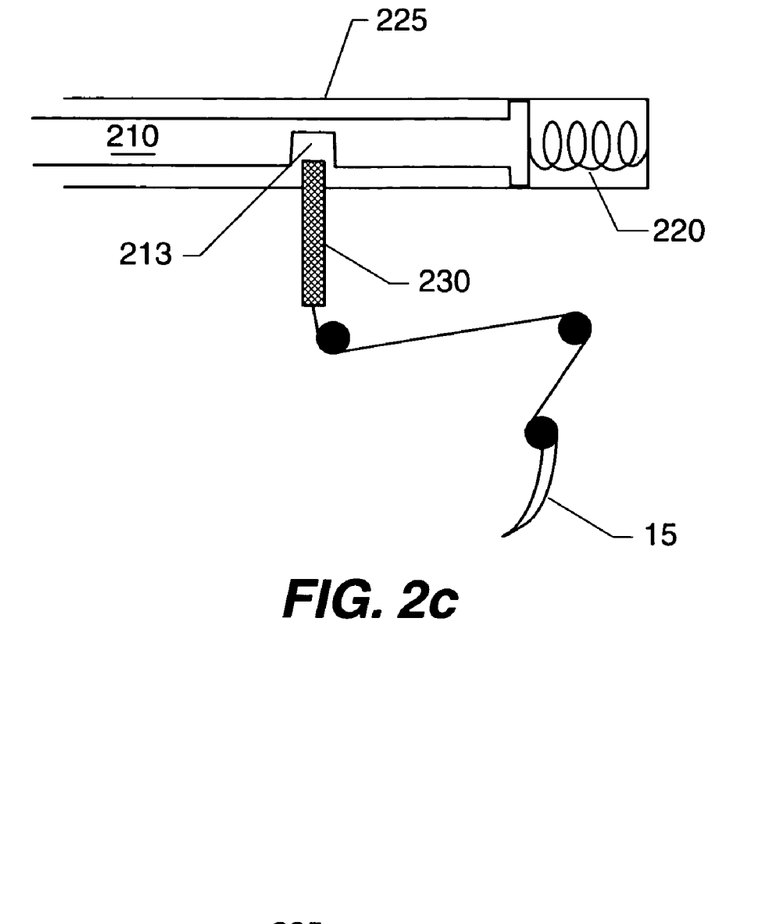

In FIG. 2c, spring 220 is compressed as sampling media member 210 is pressed into chamber 225. Latch 230 slips into notch 213. When trigger 15 is depressed, latch 230 is pulled out of notch 213 and spring 220 pushes sample media member 210 out of chamber 225.

Figure 2D:
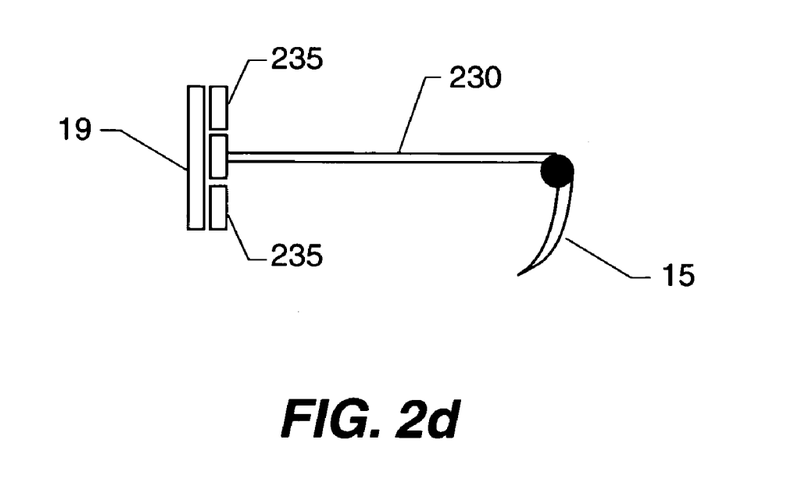

Lastly, FIG. 2d depicts trigger 15 mechanically attached to plunger 230. As trigger 15 is depressed, plunger 230 pushes sample media 19 from Velcro pad 235, or in alternative embodiments (not shown), two sided tape or magnetic strips may be used instead of Velcro.

Figure 3:
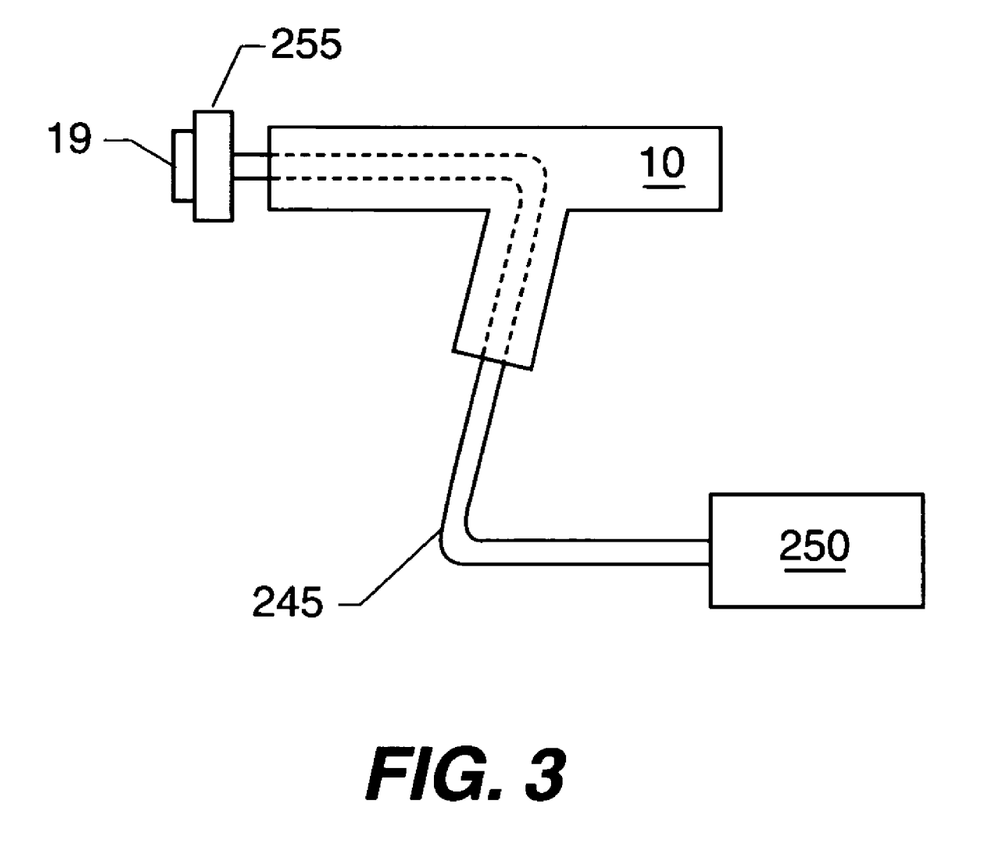
FIG. 3 is a pictorial illustration of a vacuum based universal sample media adapter.

As an alternative approach to mechanical trigger mechanisms, a vacuum-based sample media adapter may be employed to secure sample media 19 as illustrated in FIG. 3. Suction cup 255, located on the front of apparatus frame 10, is attached to body-worn vacuum pump 250 by hose 245. By activating vacuum pump 250, the operator secures sample media 19 via suction cup 255. After the sample is taken, sample media 19 is simply dropped into a storage container by turning off vacuum pump 250.

Referring back to FIG. 1, miniature camera 20 is mounted on top of the apparatus and serves two purposes: (1) to take digital photos or videos of the sampling location and sample subject, and (2) to identify the sample media and corresponding storage container by taking an image of a unique ID tag.

The live video stream from video camera 20 may be transmitted to a remote monitoring station or recorded locally. This could be used for quality assurance purposes and for the protection of sampling personnel. Remote transmission allows the exchange of information directly from a sampling scene to a centralized command and control center. The live video feed would also enable sampling network operators to generate real time geographical maps of sampling locations to ensure complete sampling coverage.

An individual ID tag, which may be affixed to sampling media 19 or a respective sample container, may be a barcode label or a handwritten note. A central processing unit (e.g., Personal Digital Assistant (PDA), hybrid PDA, Single Board Computer, Wearable Computer, or Embedded PC) running a resident barcode pattern recognition or Optical Character Recognition algorithm may link the other sample information that is generated by the handheld apparatus during the sampling process (e.g. digital photo, video, and the 3D coordinates of the sampling location) to the ID tag. The onboard, real-time data fusion capability assists in eliminating record keeping errors.

The built-in, fully automatic, electronic sample registration and record keeping provided by the apparatus relieves the operator from tedious, error prone, and time consuming sample record keeping tasks. Thus, the operator is able to concentrate on the sampling task at hand, which speeds up the sampling rate and increases the overall sampling quality.

Referring to FIG. 1, the use of PDA 30 as the computer operating system includes benefits such as relatively small dimensional characteristics and low cost (i.e., $200–$400). Software applications that run on a PDA also run on desktop PCs, allowing transfer of acquired data to office computer equipment. For example, companies like Sensory, Inc., offer special, optimized versions of speech recognition software for PDA and PC platforms. Similar to laptops and desktop PCs, PDAs include expansion slots and I/O interfaces that allow connections to virtually any peripheral unit. Commercial PDAs that may be used in the present invention apparatus include: the HP iPAQ H5550 Pocket PC, the Casio EG800 Pocket PC, the Toshiba e740 Pocket PC, the Fujitsu Siemens LOOX Pocket PC, the Mitac Mio 338 Pocket PC, and the ViewSonic V35 Pocket PC.

In another embodiment (not shown), the latest generation of hybrid cell phones may be used in place of PDA 30 and camera 20, as hybrid cell phones now include a built-in camera, web browser, and full-fledged PDA capabilities.

Figure 4:
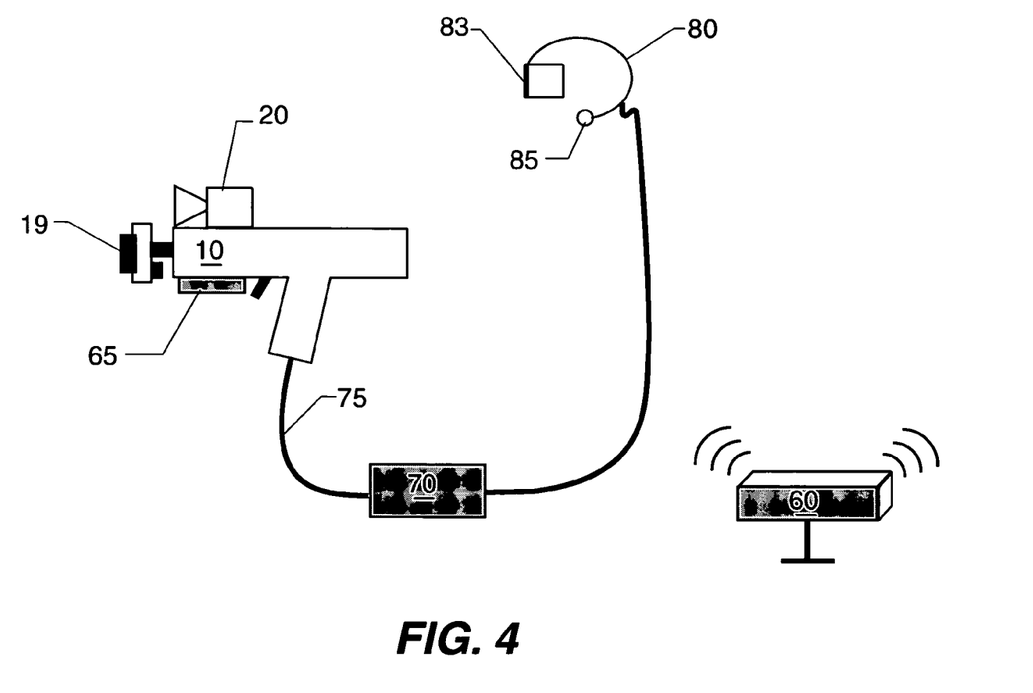
FIG. 4 is a pictorial illustration of one embodiment of the present invention that comprises a wearable computer for information processing and storage, a headset video display, and microphone.

Referring now to FIG. 4, another embodiment replaces PDA 30 shown in FIG. 1 with wearable computer 70 carried by the operator. Computer 70 can be an embedded, off-the-shelf PC104-based computer, similar to the Xybernaut MA V 256 MB Package manufactured by Xybernaut Corporation.

In yet another embodiment, the present invention may also be equipped with GPS module 40 (FIG. 1). GPS module 40 is primarily used in outdoor sampling scenarios, e.g., soil or water sampling, where a GPS signal is strongest. GPS module 40 allows for the automatic generation of electronic records with relatively precise location information (i.e. +/−1 meter). The location information provided by GPS module 40 eliminates the need for physically marking the sampling locations, which may not be possible, or useful in continuously changing sampling environments.

FIG. 4 illustrates an embodiment that may be used both indoors and underground, where GPS signals are usually not available, or where the GPS spatial resolution is not sufficient. This embodiment uses an optical, ultrasonic, or electromagnetic 3D position tracking system to identify the sampling locations.

A 3D position tracking system comprises base station 60 and one or more position tracking sensors 65 (e.g., one per sampler if there are multiple people sampling in the same area concurrently). Before the sampling task can commence, base station 60 must be strategically positioned at a reference location within the sampling area. The location of base station 60 must be recorded, as all 3D sampling location measurements are taken relative to the physical location of base station 60. After setting up base station 60, position tracking sensor(s) 65 communicate the sample location(s) via wire-based or wireless connections providing maximum sampling flexibility. Wireless, commercially available 3D position tracking systems, such as Intersense's IS-900 Mini-Trax, can achieve position measurement accuracies of +/−0.75 mm and +/− 0.05 degree angular. After recording the 3D coordinates of the sampling location, the computer operating system would then link the sample ID and any digital photos or videos of the sampling location and sample subject with the physical coordinates of the sampling location.

Most commercially available position tracking systems can be directly interfaced with the computer operating system via a standard hardware interface, such as a serial port, a parallel port, a CF (Compact Flash) card slot, a SDIO (Secure Digital I/O) card slot, or a PCMIA (Personal Computer Manufacturer Interface Adaptor) card slot.

Any embodiment of the present invention that comprises a computer, either PDA or wearable, may be equipped with additional sensors for recording relevant parameters such as ambient air pressure, humidity, PH, wind currents, sampling pressure, or the like, to create a comprehensive data set. For example, a built-in pressure sensor enables the operator to measure the pressure applied to the sample media during the sampling task, which is used for verification of applying the correct pressure. The sensor may also be connected to a red and green LED that would light up red when the pressure is outside a predetermined sampling pressure range, or green if it is within the proper pressure range.

As shown in FIG. 1, another embodiment of the present invention comprises built-in microphone 50. Microphone 50 allows the operator to operate the sampling apparatus via simple voice commands. In order too take an image or video of the sampling location with miniature camera 20, or to audio record the sampling coordinates, the operator simply speaks into microphone 50. Voice recognition software, running locally on the computer operating system, translates the simple voice commands (e.g., "Record Location" or "Read Sample ID") into the appropriate program instructions. This feature allows the operator to have one hand free for other activities. Using voice-input commands also aids in preventing contamination of the apparatus, which could occur while pushing buttons on the apparatus with a potentially contaminated glove. The voice input commands are processed in real-time with a commercially available voice-to-text translator software program, such as Sensory Inc.'s VoiceActivation™. The ability to record and execute voice command macros, which is a standard feature in most commercially available voice processor programs, enables the operator to perform complex data acquisition operations with a single command.

Referring to FIG. 4, the operator may also be equipped with lightweight head set 80. Head set 80 includes video display 83 that replaces or enhances the screen of PDA 30 shown in FIG. 1. Video display 83 can be used by the operator to identify previously sampled locations by superimposing previous sample coordinate data or video while scanning the current field of view. Head set 80 may also include microphone 85 for the voice input applications previously discussed. In case of an emergency, the operator can use a voice communication interface connected to microphone 85 to call for help. This feature significantly increases the safety and security of the sampling personnel without requiring additional communication and monitoring equipment. Miniature camera 20 and optional GPS 40 or position tracking sensors 65 are directly linked to wearable computer 70 via cable 75.

METHOD OF USE

Figure 5:
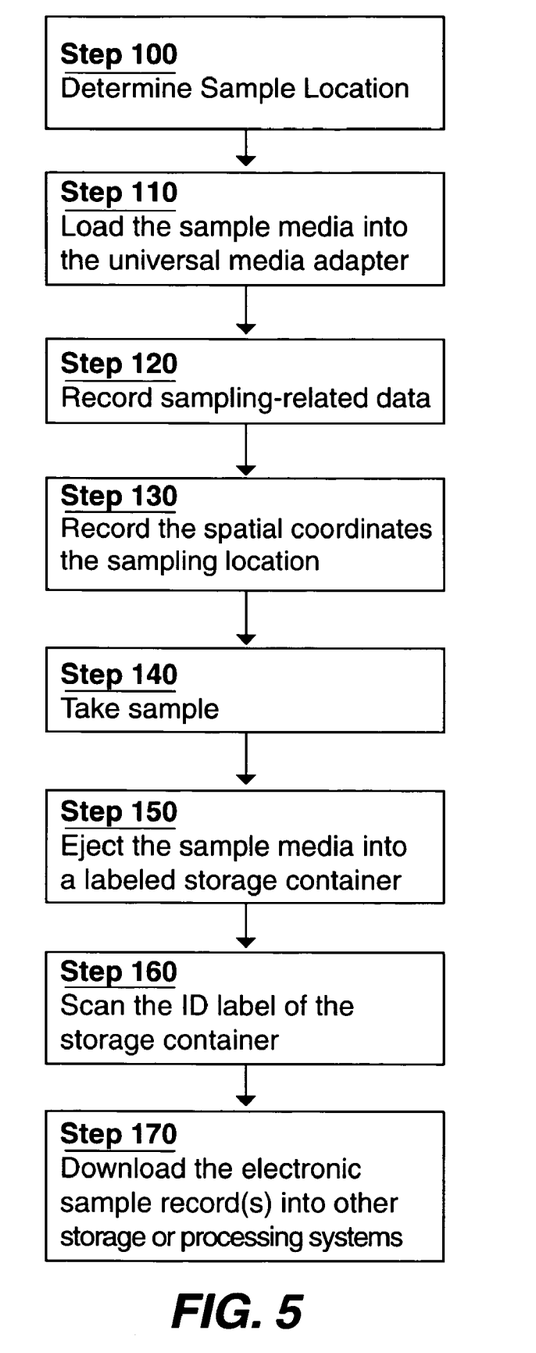
FIG. 5 is a flowchart describing the method of use for the present invention.

FIG. 5 depicts a flowchart of the method of use for the handheld sampling apparatus. It is recognized that the sample taker (operator) may use only a few of the identified steps, add new steps, or vary the order of the steps, depending on the sampling regimen. First, the sampling location is determined in Step 100. In Step 110, the operator loads the sample media into the universal media adapter. As previously discussed, the sample loading and unloading mechanism is designed such that the operator does not have to touch the sample media or sample at any point, preventing personal exposure and sample cross-contamination.

In Step 120 the operator records sampling-related data, depending on the embodiment, using either the PDA, wearable computer, camera/video, or voice recording. Information recorded may include: the operator's ID, sampling time and date, handwritten or machine-encoded identifiers of the sample media and its storage container, the sampling protocol, and still or video images of the sampling location and sampled objects.

A barcode reader may also be used for tracking information, as the camera/video in conjunction with a commercial software product, such as Codepoint™, allows for barcode scanning. For example, to scan a barcode, the operator would point the camera/video at the barcode label and take an image. Products such as Codepoint™ take this image, locate the barcode label within, and, via sophisticated image processing algorithms, extract the bar code. The extracted barcode is automatically inserted into the sample's electronic record via PDA or wearable computer. Codepoint™ uses a patented algorithm that enables it to extract barcodes even from a live video stream as well as still images. Location ID labels may also scanned at the beginning or the end of the sampling, which then would link the sample to that location.

The operator may use any of the I/O peripherals of the apparatus (e.g., built-in voice recorder or digital camera) to record additional information about the sampling location or sampled object. This additional information may be used to speed up locating the sampling point during re-sampling, if required.

In Step 130, the operator records the 2D or 3D spatial coordinates of the sampling location into data manager software application using either GPS module 40 disclosed in FIG. 1 or optical, ultrasonic, or electromagnetic 3D position tracking module 60 shown in FIG. 4. In the alternative, the operator may be resampling, and the previous recorded spatial coordinates, either from GPS or 3D tracking system, are used to identifying the original sample point.

In Step 140, the operator takes a sample with the attached sample media (e.g., a surface swipe). By using the apparatus, the sample collector avoids direct contact with the sampled object and sample material, which eliminates the potential for contact exposure and sample cross contamination.

In Step 150, with the sampling task completed, the operator uses the handheld apparatus's unloading mechanism to directly eject the sample media into a storage container. The operator then scans the ID label of the storage container using the camera and resident optical character recognition software in Step 160. Similar to the sample ID label, the storage container's ID label is correlated to the sample, sample location, sample time, etc.

In Step 170, the operator may download the electronic sample record(s), as a comprehensive data set, into other storage or processing systems, such as a Laboratory Information Management System (LIMS). Computer aided uploading of the multi-media sample data avoids manual data entry that can be both time consuming and error-prone (due to the potential for transcription errors). The fully electronic processing helps to speed up the subsequent laboratory analysis process, as the sample-related field data may be transmitted to the laboratory before the physical samples are shipped.

The foregoing description of the invention has been presented for purposes of illustration and description and is not intended to be exhaustive or to limit the invention to the precise form disclosed, and obviously many modifications and variations are possible in light of the above teaching.

The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. An apparatus for collecting a sample, comprising:
   (a) an apparatus frame sized to be held in at least one hand,
   (b) a sample media adapter that mechanically holds said sample media,
   (c) a trigger mechanism connected to said media adapter and adjacent said frame to operate said sample media adapter,
   (d) means for identifying spatial coordinates of said sample, and
   (e) means for electronically capturing, processing, and integrating sampling-related data with said spatial coordinates.

2. The apparatus of claim 1 where said means for holding a sample media comprises a suction cup connected to a vacuum pump.

3. The apparatus of claim 1 where said means for identifying spatial coordinates of said sample comprises a GPS unit.

4. The apparatus of claim 1 where said means for identifying spatial coordinates of said sample comprises a position tracking system.

5. The apparatus of claim 1 where said means for capturing, processing, and integrating said sampling related data comprises a personal digital assistant (PDA).

6. The apparatus of claim 1 where said means for capturing, processing, and integrating said sampling related data comprises a wearable computer.

7. An apparatus for taking a sample, comprising:
   (a) an apparatus frame designed to be held in at least one hand,
   (b) a sample media adapter connected to said apparatus frame and configured to hold a sample media with a securing means,
   (c) a trigger mechanism connected to said sample media adapter and adjacent said frame to operate said securing means,
   (d) a means for identifying spatial coordinates of said sample, and
   (e) a computer configured to display, receive, process, and store sampled data.

8. The apparatus of claim 7, where said computer comprises a personal digital assistant (PDA).

9. The apparatus of claim 7, where said computer comprises a wearable computer.

10. The apparatus of claim 7, further comprising a camera.

11. The apparatus of claim 10 where said camera comprises a video camera for capturing video images.

12. The apparatus of claim 7, further comprising a microphone connected to said computer.

13. The apparatus of claim 12 where said microphone is attached to a headset.

14. The apparatus of claim 7 where said means for identifying spatial coordinates comprises a GPS receiver.

15. The apparatus of claim 7 where said means for identifying spatial coordinates comprises a position tracking system.

16. The apparatus of claim 7 where said computer display is attached to a headset.

17. A method for taking a sample with a handheld sample collector, comprising:
   (a) determining a location of said sample,
   (b) allocating an individual ID for said sample,
   (c) loading a sample media into a sample media adapter,
   (d) determining spatial coordinates of said sample location, (e) using said handheld sample collector to collect said sample with said sample media, and (f) merging said individual ID with said spatial coordinates within a computer program creating a comprehensive data set.

18. The method of claim 17 further comprising scanning images of said individual ID, said sample location, and said sample with a video camera and merging said images with said comprehensive data set within said computer program.

19. The method of claim 17 further comprising downloading said comprehensive data set into data processing systems.

20. The method of claim 17 where said spatial coordinates are directly determined from a GPS signal.

21. The method of claim 17 where said spatial coordinates are determined relative to a fixed reference.

* * * * *